US012802781B2

(12) United States Patent
Hie et al.

(10) Patent No.: US 12,802,781 B2
(45) Date of Patent: *Nov. 17, 2026

(54) ESCAPE PROFILING FOR THERAPEUTIC AND VACCINE DEVELOPMENT

(71) Applicants: Brian Hie, Cambridge, MA (US); Bonnie Berger Leighton, Newtonville, MA (US); Bryan D. Bryson, Boston, MA (US)

(72) Inventors: Brian Hie, Cambridge, MA (US); Bonnie Berger Leighton, Newtonville, MA (US); Bryan D. Bryson, Boston, MA (US)

(*) Notice: Subject to any disclaimer, the term of this patent is extended or adjusted under 35 U.S.C. 154(b) by 918 days.

This patent is subject to a terminal disclaimer.

(21) Appl. No.: 17/322,649

(22) Filed: May 17, 2021

(65) Prior Publication Data

US 2022/0013194 A1 Jan. 13, 2022

Related U.S. Application Data

(63) Continuation of application No. 17/148,404, filed on Jan. 13, 2021, now Pat. No. 11,011,253.

(Continued)

(51) Int. Cl.

*G16B 40/30* (2019.01)
*G06N 3/045* (2023.01)

(Continued)

(52) U.S. Cl.

CPC ............. *G16B 40/30* (2019.02); *G06N 3/045* (2023.01); *G06N 3/088* (2013.01); *G16B 30/00* (2019.02)

(58) Field of Classification Search

CPC ........ G16B 30/00; G16B 30/10; G16B 30/20; G16B 40/00; G16B 40/10; G16B 40/20;

(Continued)

(56) References Cited

U.S. PATENT DOCUMENTS 11,386,324 B2 * 7/2022 Gao ........................ G16B 40/00
2007/0055662 A1 * 3/2007 Edelman ............... G06F 40/237

(Continued)

OTHER PUBLICATIONS

Bepler T, Berger B. Learning protein sequence embeddings using information from structure (version 1). arXiv preprint arXiv: 1902.08661. Feb. 22, 2019. (Year: 2019).*

(Continued)

*Primary Examiner* — Jesse P Frumkin

(74) *Attorney, Agent, or Firm* — David H. Judson

(57) ABSTRACT

A method of viral escape profiling is used in association with antiviral or vaccine development. The method begins by training a language-based model against training data comprising a corpus of viral protein sequences of a given viral protein to model a viral escape profile. The viral escape profile represents, for one or more regions of the given viral protein, a relative viral escape potential of a mutation, the relative viral escape potential being derived as a function that combines both "semantic change," representing a degree to which the mutation is recognized by the human immune system (i.e., antigenic change), and "grammaticality," representing a degree to which the mutation affects viral infectivity (i.e. viral fitness). Using the model, a region of the given viral protein having an escape potential of interest is identified. Information regarding the region is then output to a vaccine or anti-viral therapeutic design and development workflow.

9 Claims, 11 Drawing Sheets

Related U.S. Application Data

(60) Provisional application No. 63/049,676, filed on Jul. 9, 2020.

(51) Int. Cl.
*G06N 3/088* (2023.01)
*G16B 30/00* (2019.01)

(58) Field of Classification Search
CPC ...... G16B 40/30; G16B 99/00; G06N 3/0454; G06N 3/088
See application file for complete search history.

(56) References Cited

U.S. PATENT DOCUMENTS

| | | | | |
|---|---|---|---|---|
| 2009/0162383 | A1* | 6/2009 | Padlan | G16B 20/00 536/23.1 |
| 2021/0041454 | A1* | 2/2021 | Tsou | G16B 40/10 |
| 2021/0202043 | A1* | 7/2021 | Sudol | G16B 15/30 |
| 2022/0172055 | A1* | 6/2022 | Bileschi | G16B 20/00 |

OTHER PUBLICATIONS

Bepler T, Berger B. Learning protein sequence embeddings using information from structure (version 2). arXiv preprint arXiv: 1902.08661. Oct. 16, 2019. (Year: 2019).*

Learning the language of viral evolution and escape Brian Hie, Ellen Zhong, Bonnie Berger, Bryan Bryson. bioRxiv 2020.07.08.193946; doi: https://doi.org/10.1101/2020.07.08.193946 (Year: 2020).*

Hie, Brian , Ellen D. Zhong, Bonnie Berger, and Bryan Bryson. “Learning the language of viral evolution and escape.” Science 371, No. 6526 (2021): 284-288 (Year: 2021).*

“Major histocompatibility complex.” Merriam-Webster.com. 2025. https://www.merriam-webster.com/dictionary/major%20histocompatibility%20complex (Mar. 18, 2025) (Year: 2025).*

Bernstein, Frances C., et al. “The Protein Data Bank: a computer-based archival file for macromolecular structures.” Journal of molecular biology 112.3 (1977): 535-542. (Year: 1977).*

R. D. Finn, A. Bateman, J. Clements, P. Coggill, R. Y. Eberhardt, S. R. Eddy, A. Heger, K. Hetherington, L. Holm, J. Mistry, E. L. Sonnhammer, J. Tate, and M. Punta. Pfam: the protein families database. Nucleic Acids Res., 42(Database issue): D222â230, Jan. 2014. (Year: 2014).*

* cited by examiner

Original: australian dead in bali
Semantically closest: aussie dead in bali
CSCS change: australian *ballet* in bali Original: blast off of apollo 8
Semantically closest: blast off of apollo 13
CSCS change: blast *victims* of apollo 8

Original: winegrowers revel in good season
Semantically closest: winegrowers revel in strong season
CSCS change: winegrowers revel in *flu* season NOUN VERB NOUN
Original: nauru bans transhipments to tackle overfishing
Semantically closest: nauru bans transhipments to combat overfishing
ADJ NOUN VERB
CSCS change: nauru bans *continue* to tackle overfishing

FIG. 1C

ESCAPE PROFILING FOR THERAPEUTIC AND VACCINE DEVELOPMENT

STATEMENT OF FEDERALLY SPONSORED RESEARCH OR DEVELOPMENT

No part of the claimed subject matter was made with government support.

TECHNICAL FIELD

This application relates generally to techniques to facilitate antiviral and vaccine development.

BACKGROUND

The ability for viruses to mutate and evade the human immune system and cause infection, called viral escape, remains an obstacle to development of antiviral therapies, as well as and vaccines. For example, viral mutations that allow an infection to escape from recognition by neutralizing antibodies have prevented the development of a universal antibody-based vaccine for influenza or human immunodeficiency virus (HIV) and are a concern in the development of therapies for severe acute respiratory syndrome coronavirus 2 (SARS-CoV-2) infection. Escape has motivated high-throughput experimental techniques that perform causal escape profiling of all single-residue mutations to a viral protein. Such techniques, however, require substantial effort to profile even a single viral strain and testing the escape potential of many (combinatorial) mutations in many viral strains remains infeasible.

There remains a need to provide new technical approaches to predict viral escape mutations to enable rapid antiviral and vaccine development. The techniques of this disclosure address this technical problem.

BRIEF SUMMARY

According to this disclosure, viral escape is modeled with machine learning algorithms originally developed for human natural language. The approach herein enables rapid, efficient and accurate identification of particular escape mutations as those that preserve viral infectivity but cause a virus to look different to the immune system, akin to word changes that preserve a sentence's grammaticality but change its meaning.

A method of viral escape profiling according to this disclosure is used in association with antiviral therapeutic or vaccine design and development workflows and systems. The method begins by training a language-based model against training data comprising a corpus of viral protein sequences of a given viral protein to model a viral escape profile of the given viral protein. The corpus of viral protein sequences of the given viral protein comprises copies of amino acid sequences, preferably from multiple host species, and the language-based model may be trained in an unsupervised manner, without data about known escape mechanisms. The viral escape profile (a model) represents, for one or more regions of the given viral protein, a relative viral escape potential of a mutation (a single one, or a combinatorial), the relative viral escape potential being derived as a function that combines both "semantic change," representing a degree to which the mutation is recognized by the human immune system (i.e., antigenic change), and "grammaticality," representing a degree to which the mutation affects viral infectivity (i.e. viral fitness). The notions of semantic change and grammaticality derive from their analogues in natural language processing. Using the model, a region of the given viral protein having an escape potential of interest is then identified. Information regarding the region is then output to a vaccine or anti-viral therapeutic design and development workflow. For example, when the escape potential of interest is a low escape potential, the region is targeted for vaccine development; when the escape potential of interest is a high escape potential, the region is targeted for anti-viral therapeutic development.

In one representative, but non-limiting implementation, the language-based model comprises a Bi-directional Long Short-Term Memory (BiLSTM) architecture, a deep learning neural network that comprises a set of hidden layers, and an output layer. In this implementation, semantic change is encoded as distances in an embedding space in the set of hidden layers, and grammaticality is an emitted probability output from the output layer. Other deep learning techniques (e.g., transformer-based approaches, such as GTL-3) may be used to train the model in lieu of recurrent architectures.

In a specific embodiment, the given viral protein is one of: influenza hemagglutinin, HIV Env, and SARS-CoV-2 Spike.

The foregoing has outlined some of the more pertinent features of the subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the subject matter and the advantages thereof, reference is now made to the following descriptions taken in conjunction with the accompanying drawings, in which:

FIG. 1C depicts how CSCS-proposed changes to an English language headline makes large changes to the overall semantic meaning of a sentence or to the part-of-speech structure;

DETAILED DESCRIPTION

According to this disclosure, language modeling is used to shed light on those parts of a protein not prone to escape, thereby enabling more-targeted vaccine and anti-viral design and development. As will be described, the approach herein trains an algorithm that learns to model escape, preferably from viral sequence data alone. It is not unlike learning properties of natural language from large text corpuses, since languages like English and Japanese use sequences of words to encode complex meanings and have complex rules (e.g., grammar). To escape, a mutant virus must preserve infectivity and evolutionary fitness, i.e., it must obey a "grammar" of biological rules, and the mutant must no longer be recognized by the immune system, analogous to a change in the "meaning" or the "semantics" of the virus. As will be seen, the technique of this disclosure models viral escape preferably by characterizing both semantic change and grammaticality. More specifically, the approach (sometimes referred to herein as Constrained Semantic Change Search (CSCS) for viral escape prediction is designed to search for mutations to a viral sequence that preserve fitness while being antigenically different. This corresponds to a mutant sequent that is grammatical (i.e., conforms to the structure and rules of a language), but has high semantic change with respect to the original (e.g., wildtype) sequence.

Figure 1A:
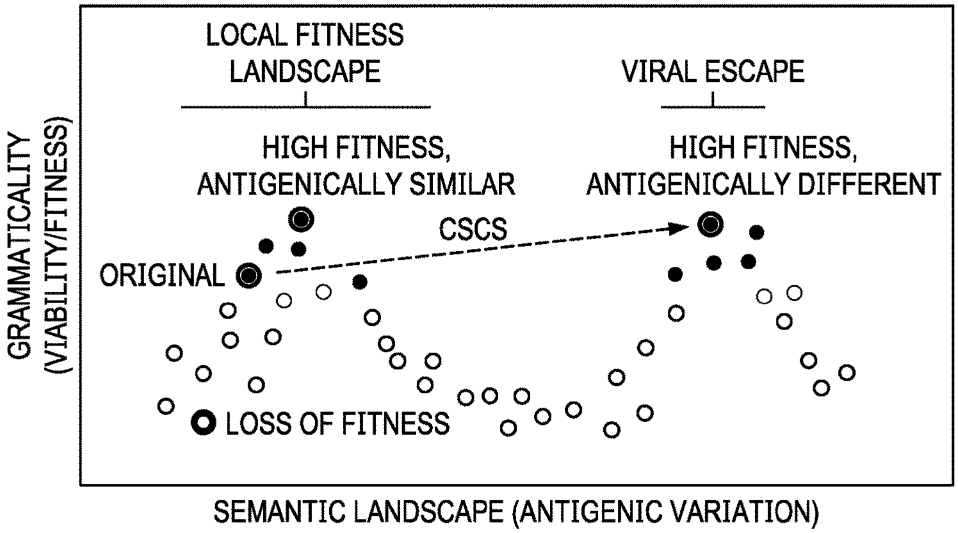
FIG. 1A depicts a plot of viability/fitness (grammaticality) versus antigenic variation (semantic landscape) showing how constrained semantic change search (CSCS) for viral escape prediction is used to search for mutations to a viral sequence that preserve fitness while being antigenically different.

Currently, computational models of protein evolution focus either on fitness or on functional/semantic similarity, whereas the approach herein (as depicted in FIG. 1A) preferably understands both. Rather than developing two separate models of fitness and function, preferably a single neural language model is used that simultaneously achieves these tasks. In one preferred implementation (although not necessarily limiting), a neural language model with a bidirectional long short-term memory (BiLSTM) architecture is used to learn both semantics (e.g., as a hidden layer output) and grammaticality to predict escape. FIG. 1C provides an example of this approach with respect to several natural language statements. As the examples in FIG. 1C show, CSCS-proposed changes to a news headline (implemented using a neural language model trained on English news headlines) makes large changes to the overall semantic meaning of a sentence or to the part-of-speech structure. The semantically-closest mutated sentence according to the same model, however, is largely synonymous with the original headline. The language model learns the probability of a token (e.g., an English word) given its sequence context (e.g., a sentence). Internally, the language model constructs a semantic representation, or an "embedding," for a given sequence, and the output of the language model encodes how well a particular token fits within the rules of the language, or grammaticality and (as used herein) can also be thought of as "syntactic fitness." According to this disclosure, the principles used to train a language model on a sequence of English words are used to train a language model on a sequence of amino acids. Although immune selection occurs on phenotypes (e.g., protein structures), evolution dictates that selection is reflected within genotypes (e.g., protein sequences), which—according to this disclosure—language models leverage to learn functional properties from sequence variation.

Thus, in the approach herein, language model-encoded semantic change corresponds to antigenic change, language model grammaticality captures viral fitness, and both high semantic change and grammaticality predict viral escape. The CSCS task search for mutations with both high grammaticality and high semantic change. Advantageously, the preferred language model implementation of CSCS as described herein uses sequence data alone (which is easier to obtain than structure) and requires no explicit escape information (i.e. is completely unsupervised), it does not rely on multiple sequence alignment (MSA) preprocessing (i.e., it is alignment-free), and it captures global relationships across an entire sequence (e.g., because word choice at the beginning of a sentence can influence word choice at the end).

Intuitively, a goal of the approach herein is to identify mutations that induce high semantic change (e.g., a large impact on biological function) while being grammatically acceptable (e.g., biologically viable). More precisely, assume a sequence of tokens defined as $$x \stackrel{def}{=} (x_1, \ldots, x_N)$$

such that $x_i \in \mathcal{X}$, $i \in [N]$, where $\mathcal{X}$ is a finite alphabet (e.g., characters or words for natural language, or amino acids for protein sequence). Let $\tilde{x}_i$ denote a mutation at position i and the mutated sequence as $$x[\tilde{x}_i] \stackrel{def}{=} (\ldots, x_{i-1}, \tilde{x}_i, x_{i+1}, \ldots).$$

The approach first requires a semantic embedding $$z \stackrel{def}{=} f_s(x),$$

where $f_s: \mathcal{X}^N \rightarrow \mathbb{R}^K$ embeds discrete-alphabet sequences into a K-dimensional continuous space, where, ideally, closeness in embedding space would correspond to semantic similarity (e.g., more similar in meaning). Then, denote semantic change as the distance in embedding space, i.e., $$\Delta z[\tilde{x}_i] \stackrel{def}{=} \|z - z[\tilde{x}_i]\| = \|f_s(x) - f_s(x[\tilde{x}_i])\| \quad (1)$$

where $\|\cdot\|$ denotes a vector norm. The grammaticality of a mutation is described by $$p(\tilde{x}_i|x) \quad (2)$$

which takes values close to zero if $x[\tilde{x}_i]$ is not grammatical and close to one if it is grammatical. A mutation is considered grammatical if it conforms to the rules (e.g., morphology and syntax) within a given language; violation of these rules results in a loss of grammaticality.

An objective of the approach herein combines semantic change and grammaticality. Taking inspiration from upper confidence bound acquisition functions in Bayesian optimization (42), terms (1) and (2) are combined with a weight parameter $\beta \in [0, \infty)$ above to compute:

$$a(\tilde{x}_i; x) \overset{def}{=} \Delta z[\tilde{x}_i] + \beta p(\tilde{x}_i \mid x)$$

for each possible mutation $\tilde{x}_i$. Mutations $\tilde{x}_i$ are prioritized based on $\alpha(\tilde{x}_i; x)$; this ranking of mutations based on semantic change and grammaticality is sometimes referred to herein as CSCS.

Algorithms

Algorithms for CSCS potentially take many forms; for example, separate algorithms could be used to compute $\Delta z[\tilde{x}_i]$ and $p(\tilde{x}_i|x)$ independently, or a two-step approach might be possible that computes one of the terms based on the value of the other.

Instead, a preferred technique herein uses a single approach that computes both terms simultaneously and, in particular, based on learned language models that learn the probability distribution of a word given its context. One language model considers the full sequence context of a word and learns a latent variable probability distribution $\hat{p}$ and function $\hat{f}_s$ over all $i \in [N]$ where:

$$\hat{p}(x_i|x_{[N]\setminus\{i\}}, \hat{z}_i) = \hat{p}(x_i|\hat{z}_i) \text{ and } \hat{z}_i = \hat{f}_s(x_{[N]\setminus\{i\}}),$$

i.e., latent variable $\hat{z}_i$ encodes the sequence context $$x_{[N]\setminus\{i\}} \overset{def}{=} (\ \ldots\ , x_{i-1}, x_{i+1}, \ \ldots\ )$$

such that $x_i$ is conditionally independent of its context given the value of $\hat{z}_i$.

Different aspects of the language model are then to describe semantic change and grammaticality, e.g., by setting terms (1) and (2) as:

$$\Delta z[\tilde{x}_i] \overset{def}{=} \|\hat{z} - \hat{z}[\tilde{x}_i]\|_1 \text{ and } p(\tilde{x}_i \mid x) \overset{def}{=} \hat{p}(\tilde{x}_i \mid \hat{z}_i)$$

where $$\hat{z} \overset{def}{=} \frac{1}{N}\sum_{i=1}^{N} \hat{z}_i$$

is tile average embedding across all positions, $\hat{z}[\tilde{x}_i]$ is defined similarly but for the mutated sequence, and is the $\|\cdot\|_1$ is the $\ell_1$ norm, chosen because of more favorable properties compared to standard distance metrics, although some other metric may be utilized.

Effectively, distances in embedding space approximate semantic change, and the emitted probability approximates grammaticality. As used herein, the emitted probability is called "grammaticality" because in natural language tasks, it tends to be high for grammatically correct sentences. In the case of viral sequences, the training distribution consists of viral proteins that have evolved for high fitness/virality, so the approach herein hypothesizes that high grammaticality corresponds to high viral fitness, but they have been found to have good empirical support.

Figure 1B:
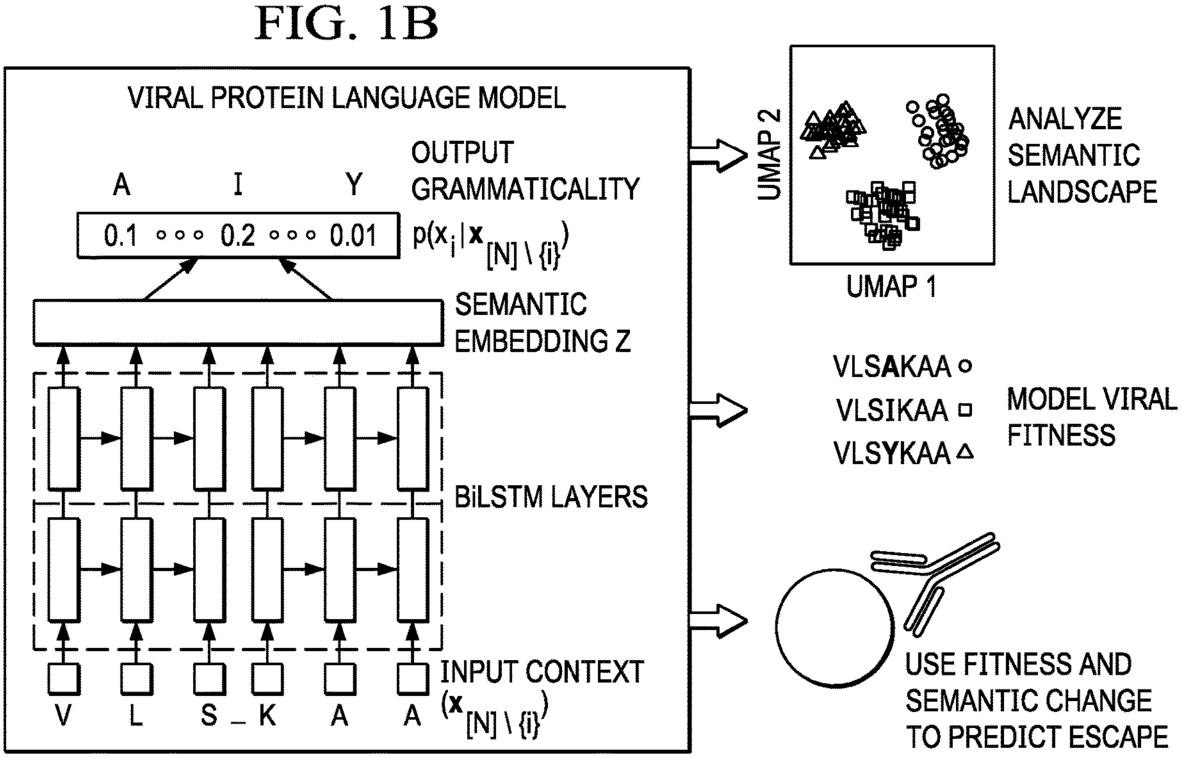
FIG. 1B depicts a viral protein-based language model according to the techniques of this disclosure and, in particular, a neural language model with a bidirectional long short-term memory (BiLSTM) architecture used to learn both semantics (as a hidden layer output) and grammaticality (as the language model output)

As recurrent architectures for protein-sequence representation learning are known and useful there, similar encoder models preferably are utilized here for the viral protein sequences One example embodiment is depicted in FIG. 1B, which is Bi-directional Long Short-Term Memory. The model passes the full context sequence into BiLSTM hidden layers. The concatenated output of the final LSTM layers is used as the semantic embedding, i.e., $$\hat{z}_i \overset{def}{=} \left[LSTM_f(g_f(x_1, \ \ldots\ , x_{i-1}))^T \ \ldots\ LSTM_r(g_r(x_{i+1}, \ \ldots\ , x_N))^T\right]^T$$

where $g_f$ is the output of the preceding forward-directed layer, $LSTM_f$ is the final forward-directed LSTM layer, and $g_r$ and $LSTM_r$ are the corresponding reverse-directed components. The final output probability is a softmax-transformed linear transformation of $\hat{z}_i$, i.e., $$\hat{p}(x_i \mid \hat{z}_i) \overset{def}{=} softmax(W\hat{z}_i + b)$$

for some learned model parameters W and b. In one particular implementation, the following constraints were used: a 20-dimensional learned dense embedding for each element in the alphabet $\mathcal{X}$, two BiLSTM layers with 512 units, and categorical cross entropy loss optimized with a learning rate of 0.001, $\beta_1$=0.9, and $\beta_2$=0.999. Hyperparameters and architecture were selected based on a small-scale grid search.

Rather than acquiring mutations based on raw semantic change and grammaticality values, which may be on very different scales, calibrating $\beta$ may be made easier in practice by first rank-transforming the semantic change and grammaticality terms, i.e., acquiring based on $$a'(\tilde{x}_i; x) \overset{def}{=} \text{rank}(\Delta z[\tilde{x}_i]) + \beta\text{rank}(p(\tilde{x}_i \mid x))$$

In this variant, all possible mutations $\tilde{x}_i$ are then given priority based on the corresponding values of $a'(\tilde{x}_i; x)$, from highest-to-lowest. Empirical results have been shown to be consistently well-calibrated around $\beta$=1 (equally weighting both terms), although this is not a requirement.

Extension to Combinatorial Mutations

For simplicity, the above description is limited to the setting in which mutations are assumed to be single-token. This is not a limitation, however, as the approach may be extended to handle combinatorial mutations. According to this variant, a mutant sequence as $\tilde{x}=(\tilde{x}_1, \ldots, \tilde{x}_N)$, which has the same length as x, where the set of mutations consists of the tokens in $\tilde{x}$ that disagree with those at the same position in x, which is denoted:

$$\mathcal{M}(x, \tilde{x}) \overset{def}{=} \{\tilde{x}_i \mid \tilde{x}_i \neq x_i\}.$$

The semantic embedding is then simply computed as $f_s(\tilde{x})$ from which semantic change is then computed as above. For the grammaticality score, a simple modeling assumption is made and grammaticality computed as:

$$\prod_{\tilde{x}_i \in \mathcal{M}(x,\tilde{x})} p(\tilde{x}_i \mid x),$$

i.e., the product of the probabilities of the individual point-mutations (implemented in the log domain for better numerical precision). This approach works well empirically in the combinatorial fitness datasets, even when the number of mutations is not fixed (e.g., as in the SARS-CoV-2 DMS Kd dataset). Other ways of estimating joint, combinatorial grammaticality terms while preserving efficient inference may also be implemented.

In viral sequences, insertions and deletions are rarer than substitutions. Nevertheless, the algorithms herein may also be extended to compute semantic change of sequences with insertions or deletions.

Figure 2A:
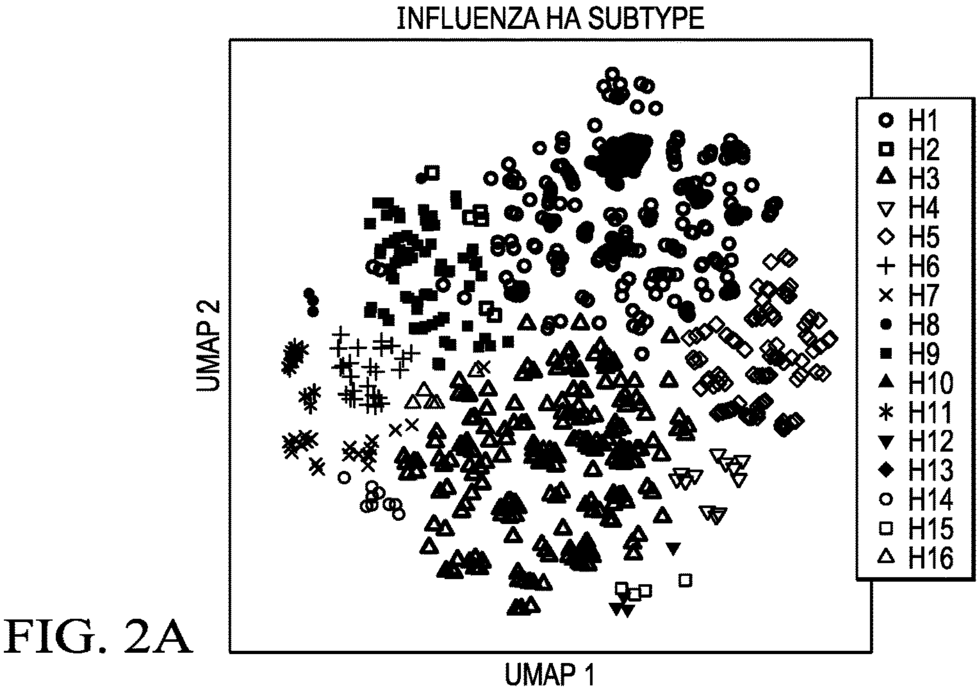
FIG. 2A depicts a UMAP visualization of the high-dimensional semantic embedding landscape of influenza HA subtype.
Figure 2B:
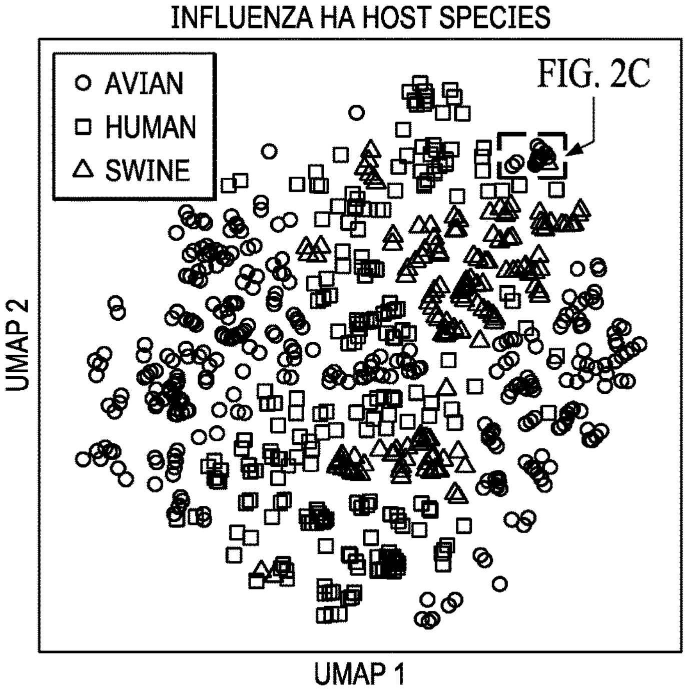
FIG. 2B depicts a UMAP visualization of the high-dimensional semantic embedding landscape of influenza HA host species.
Figure 2C:
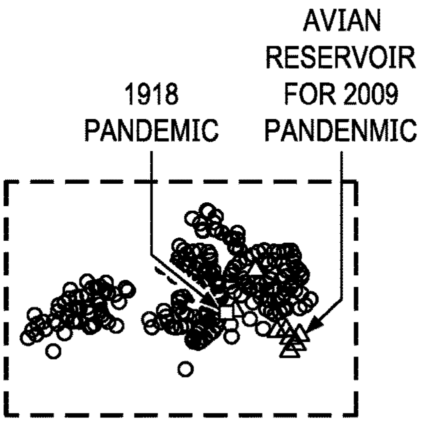
FIG. 2C is a portion of FIG. 2B enlarged to show a cluster consisting of avian sequences from the 2009 flu season onwards also contains the 1918 pandemic flue sequence.
Figure 2D:
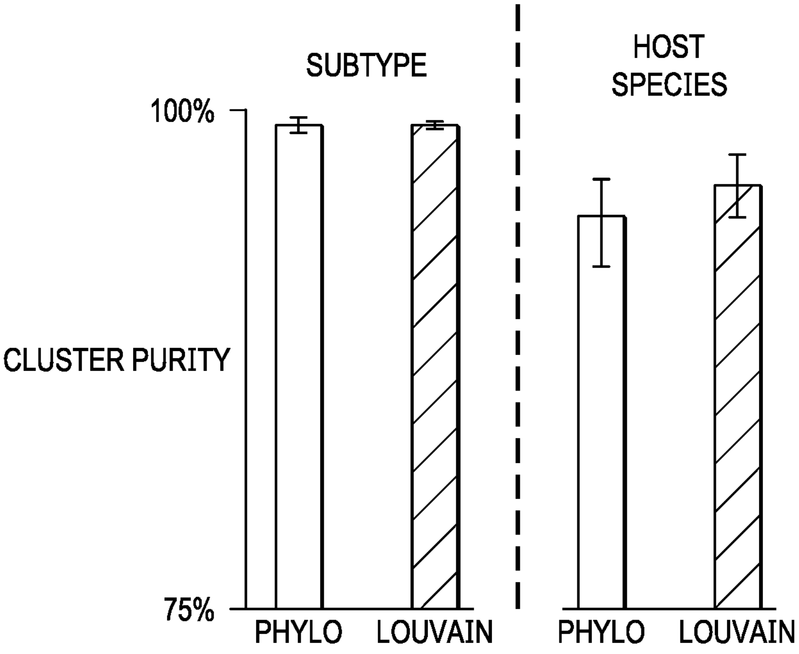
FIG. 2D depicts Louvain clusters of the HA semantic embeddings.
Figure 2E:
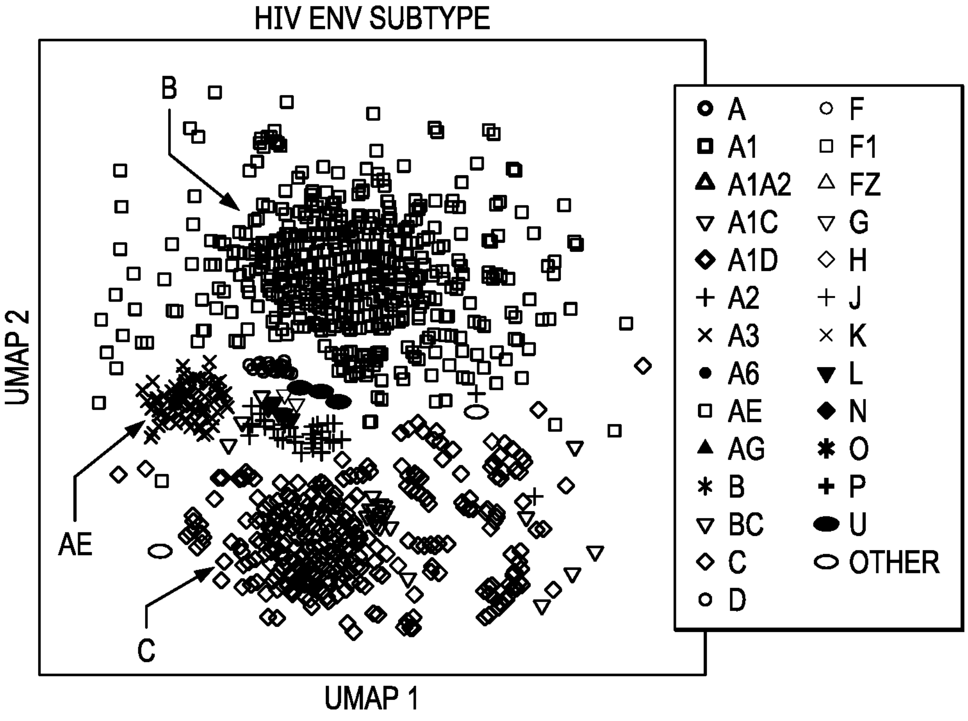
FIG. 2E depicts the HIV Env semantic landscape and, in particular, the subtype-related distributional structure)
Figure 2F:
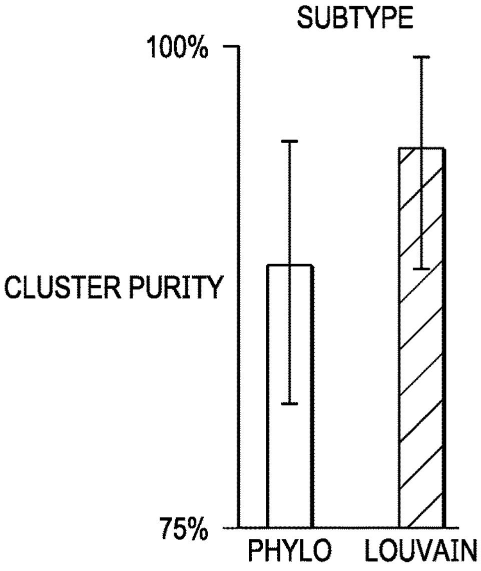
FIG. 2F depicts the Louvain clustering purity for the HIV Env subtype in FIG. 2E.
Figure 2G:
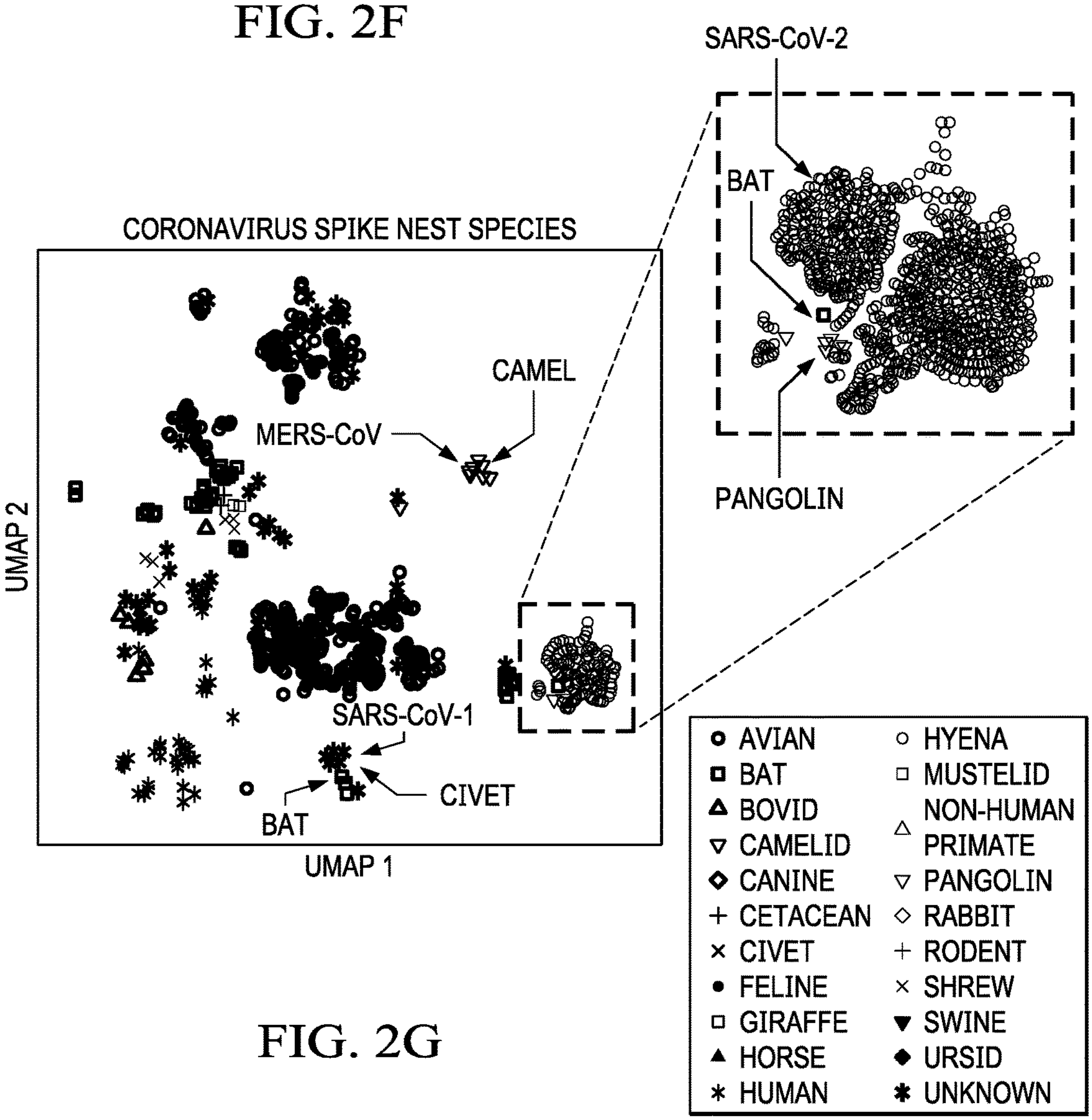
FIG. 2G depicts coronavirus spike host species; the call-out portion shows sequence proximity in the semantic landscape of coronavirus spike proteins is consistent with the possible zoonotic origin of SARS-CoV-1, MERS-CoV, and SARS-CoV-2.

Semantic patterns learned by the above-described viral language models are antigenically meaningful. This can be seen by visualizing the semantic embedding of each sequence, e.g., in the influenza, HIV and coronavirus corpuses, using Uniform Manifold Approximation and Projection (UMAP), and quantifying these clustering patterns using Louvain clustering to group sequences on the basis of their semantic embeddings. The resulting two-dimensional semantic landscapes show clustering patterns corresponding to subtype, host species of both, suggesting that the language model is able to learning functionally meaningful patterns from raw sequence. In particular, FIG. 2A (influenza HA subtype) and FIG. 2B (influenza HA host species) depict UMAP visualization of the high-dimensional semantic embedding language of influenza HA. FIG. 2C depicts a cluster consisting of avian sequences from the 2009 flu season onwards also contains the 1918 pandemic flu sequence, consistent with their antigenic similarity. As depicted in FIG. 2D, Louvain clusters of the HA semantic embeddings have similar purity with respect to subtype or host species as compared to phylogenetic sequence clustering (Phylo). In these plots bar height is the mean and error bars show 95% confidence. FIG. 2E depicts the HIV Env semantic landscape (subtype-related distributional structure), and FIG. 2F depicts its high Louvain clustering purity. FIG. 2G depicts coronavirus spike host species; as shown, sequence proximity in the semantic landscape of coronavirus spike proteins is consistent with the possible zoonotic origin of SARS-CoV-1, MERS-CoV, and SARS-CoV-2. The clustering purity based on the percent composition of the most represented metadata category (sequence subtype or host species) within each cluster can be measured. In these examples, average cluster purities for HA subtype, HA host species, and Env subtype are 99%, 96% and 95%, respectively, comparable to or higher than the clustering purities obtained by MSA-based phylogenetic reconstruction. Analysis of these semantic landscapes supports the hypothesis that viral sequence embeddings encode functional and antigenic variation.

Figure 3A:
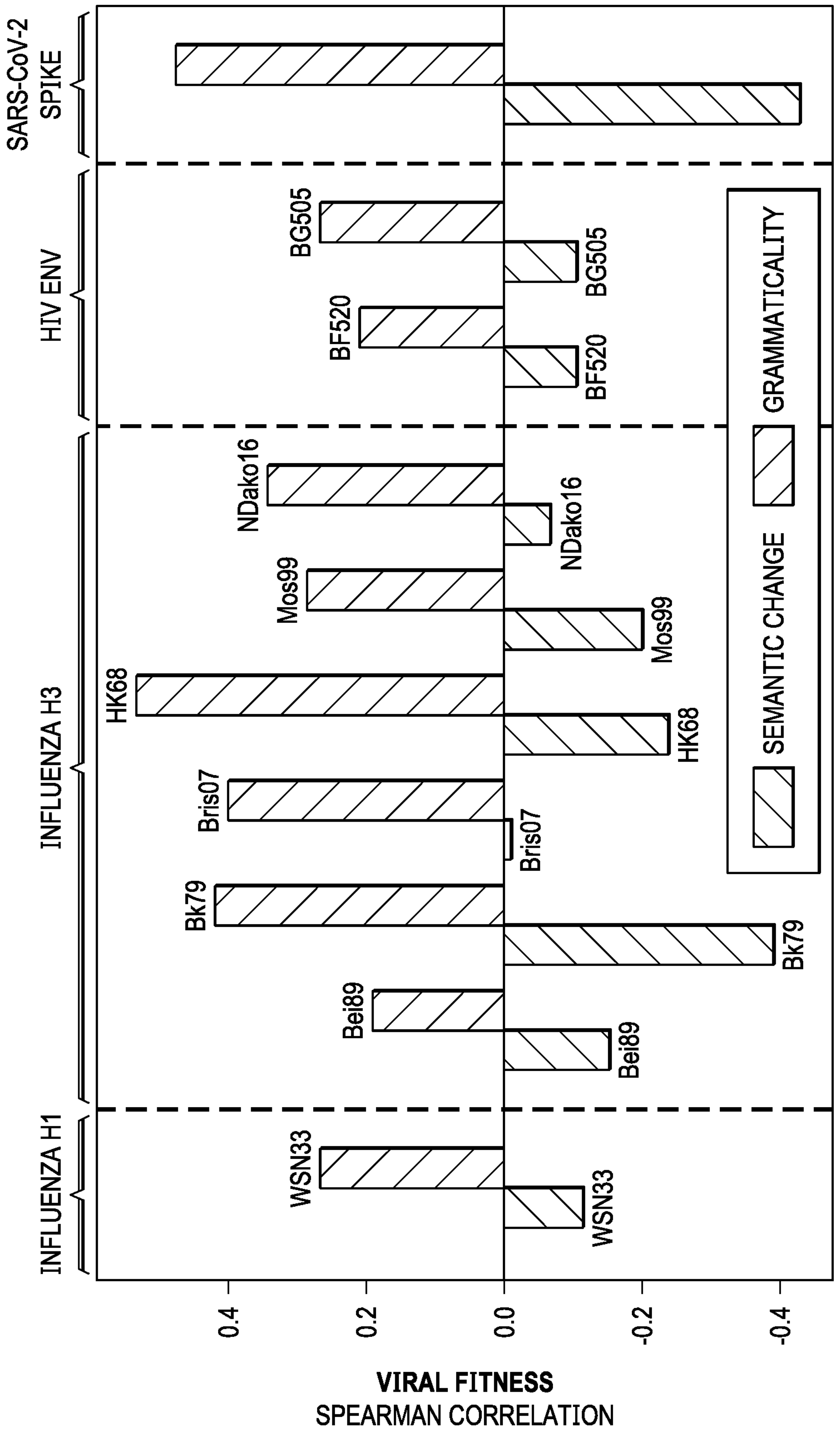
FIG. 3A depicts semantic change and grammaticality for several viral proteins.
Figure 3B:
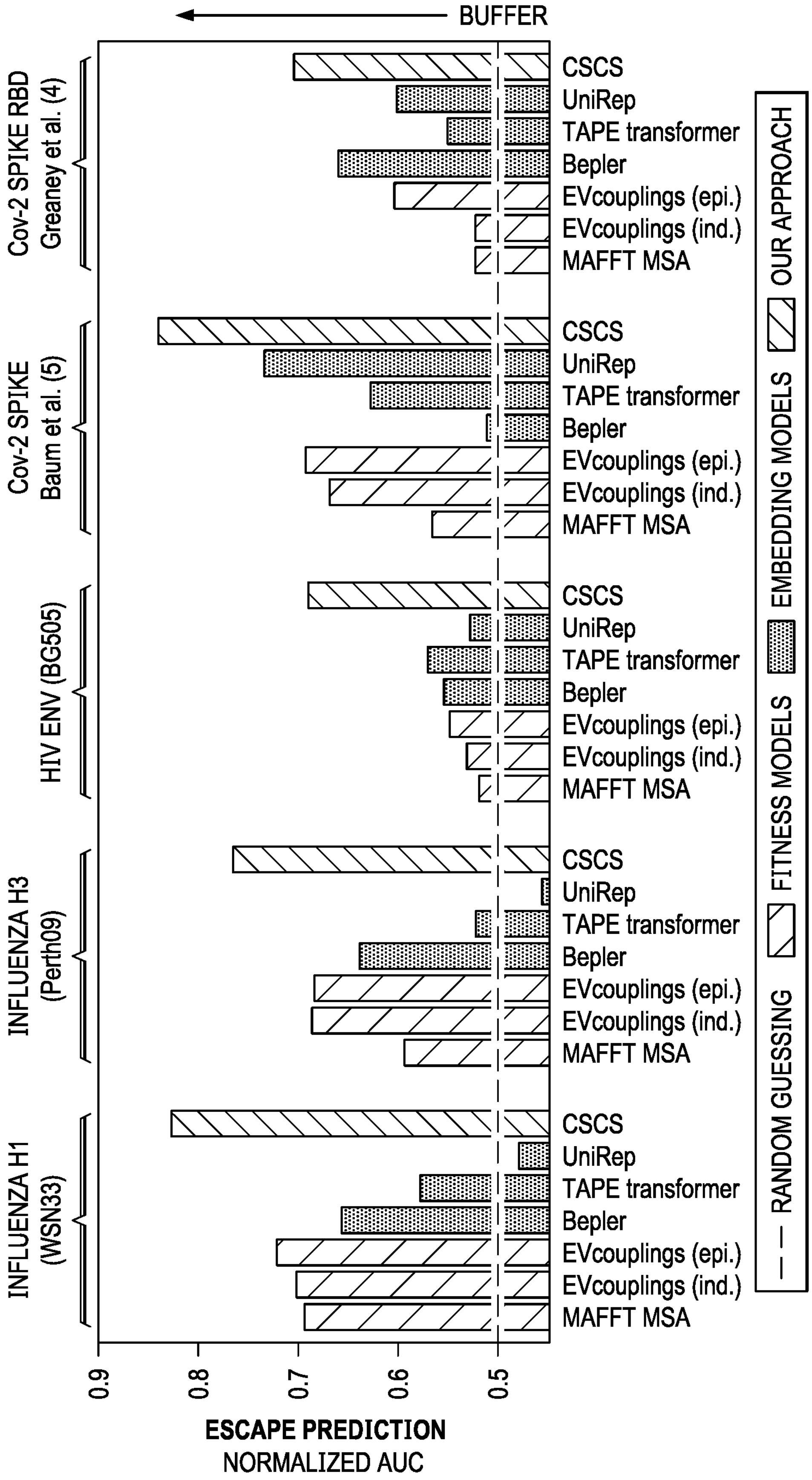
FIG. 3B shows how CSCS compares with other known techniques.
Figure 3C:
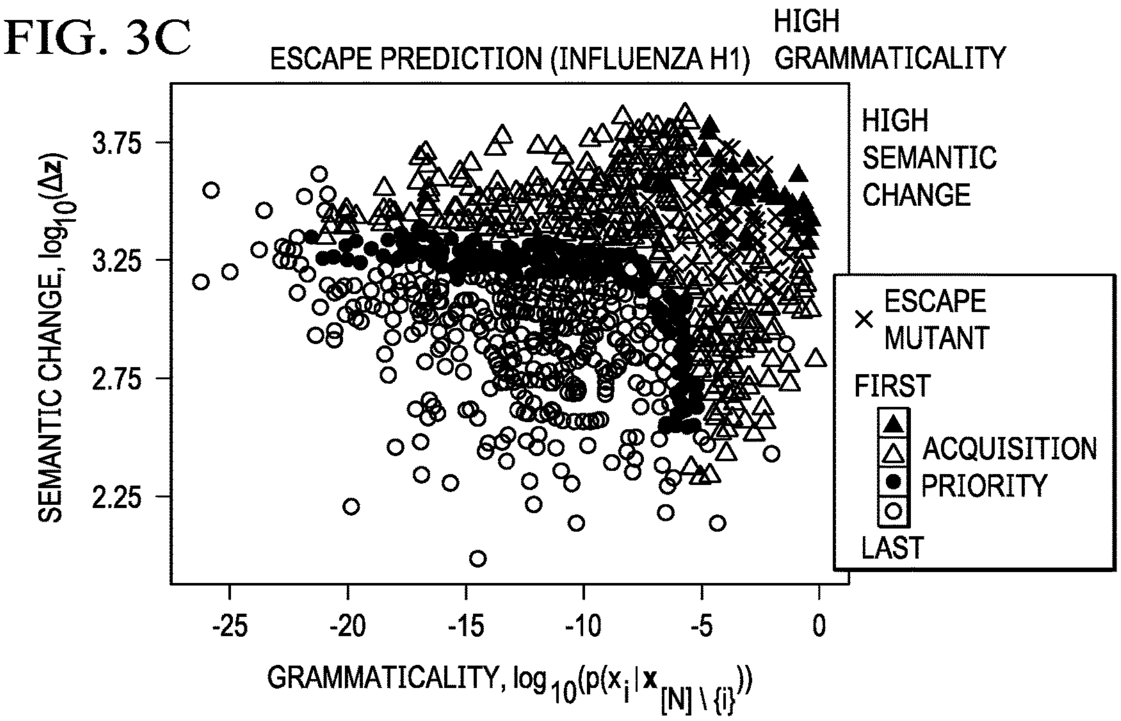
FIG. 3C depicts an escape potential plot of semantic change versus grammaticality for influenza H1.
Figure 3D:
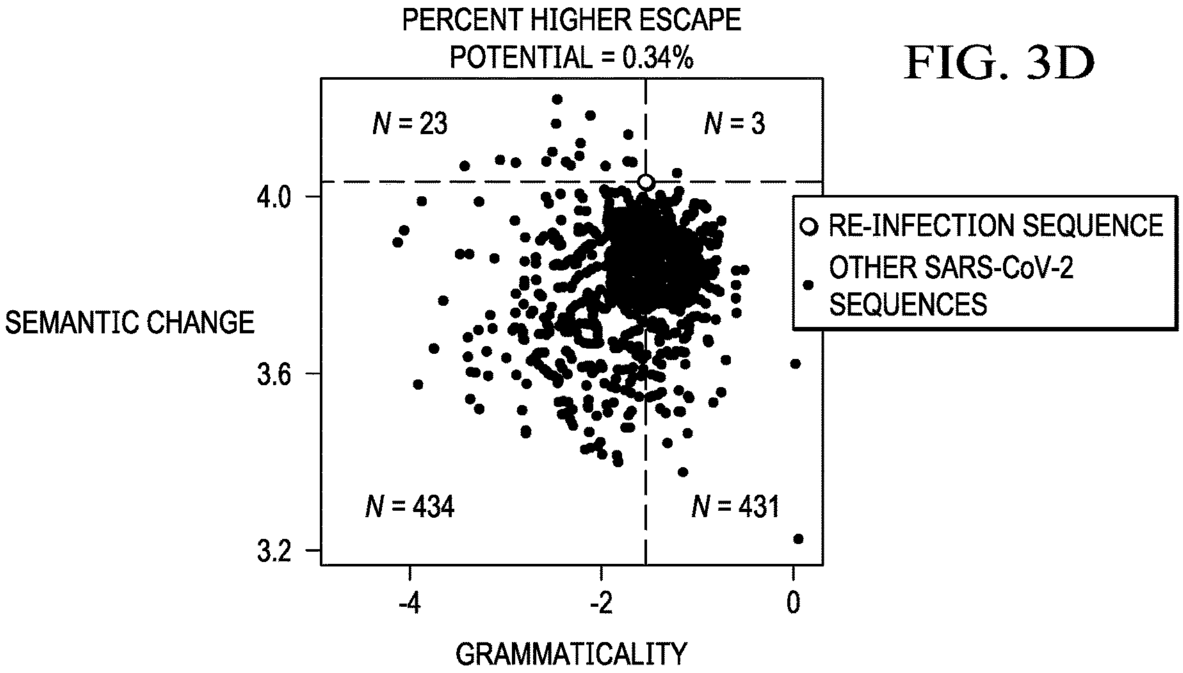
FIG. 3D is a plot of semantic change versus grammaticality across 891 surveilled SARS-CoV-2 Spike sequences.

According to this disclosure, biological interpretation of language model semantics and grammaticality enables robust escape prediction. In particular, and with reference to FIG. 3A, while grammaticality is positively correlated with fitness, semantic change has negative correlation, suggesting that most semantically-altered proteins lose fitness. As depicted in FIGS. 3B and 3C, however, a mutation with both high semantic change and high grammaticality is more likely to induce escape. Considering both semantic change and grammaticality according to the techniques herein enables identification of escape mutants that is consistently higher than that of previous fitness models or generic functional embedding models. FIG. 3D is a plot of semantic change versus grammaticality across 891 surveilled SARS-CoV-2 Spike sequences; only three have both higher semantic change and grammaticality than a Spike sequence with four mutations that is associated with a potential re-infection case.

Figure 4:
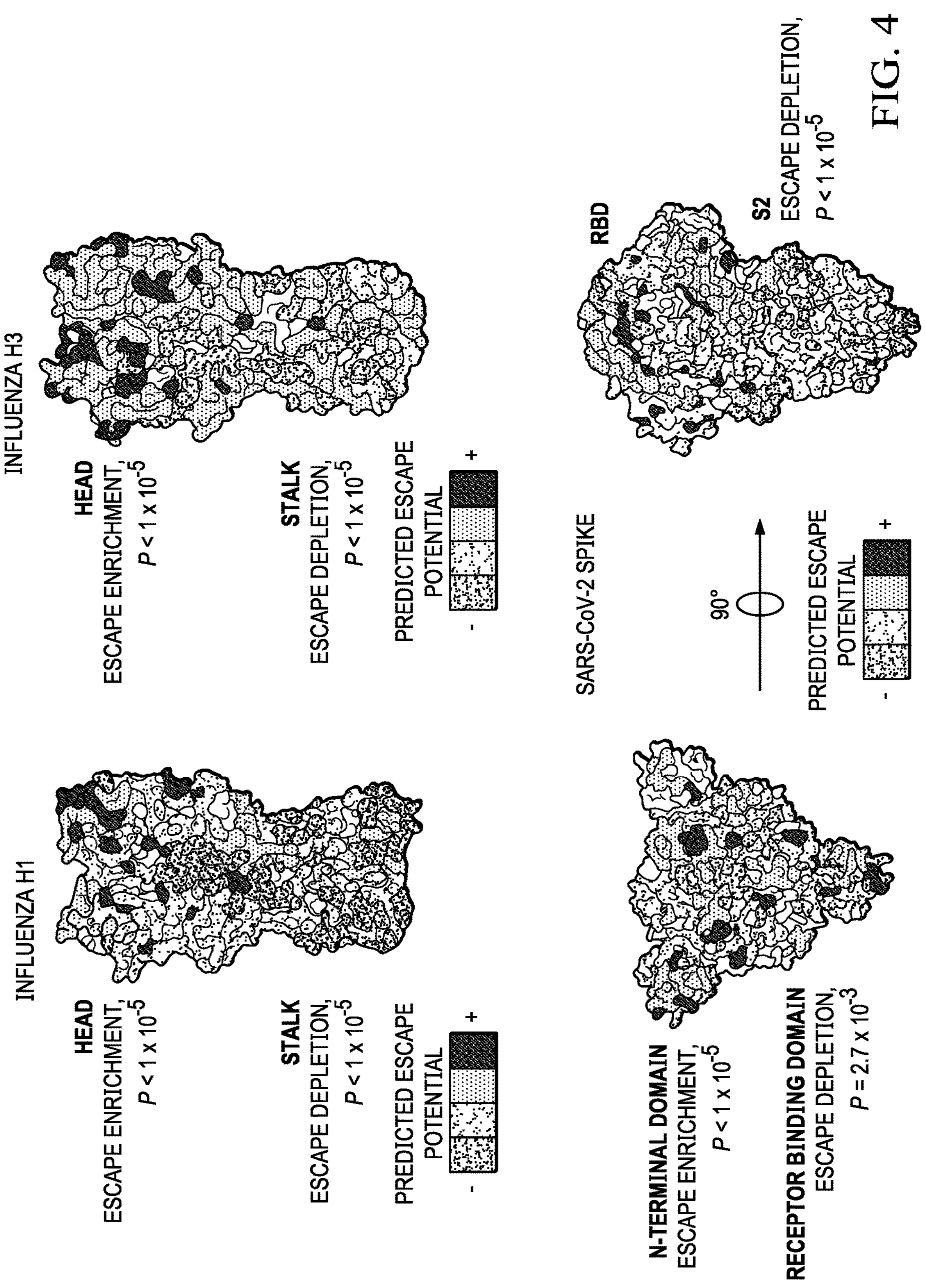
FIG. 4 depicts protein structure visualizations for influenza H1 and H3, and for the SARS-Cov-2 Spike, showing how language modeling identifies those parts of a protein that are not prone to escape.

Based on the results of CSCS technique as described, escape potential across the protein structure can then be visualized, and enrichment or depletion of escape can then be quantified. This enables identification of target regions (or sub-regions) of the protein structure that are less (or more) prone to escape, and thus facilitate the rapid design and development of therapeutics and vaccines that target those specific regions or sub-regions. FIG. 4 depicts protein structure visualizations for influenza H1 and H3, and for the SARS-Cov-2 Spike. As can be seen, escape potential is significantly enriched in the HA head (permutation-based $P<1\times10^{-5}$) and significantly depleted in the HA stalk (permutation-based $P<1\times10^{-5}$), which is consistent with HA mutation rates and supported by the successful development of anti-stalk broadly neutralizing antibodies. Escape in SARS-Cov-2 Spike is significantly enriched at the N-terminal domain and receptor binding domain (RBD) and significantly depleted at multiple regions in the S2 subunit; this model of Spike escape thus suggests that immunodominant antigenic sites in S2 may be more stable target antibody epitopes.

Figure 5A:
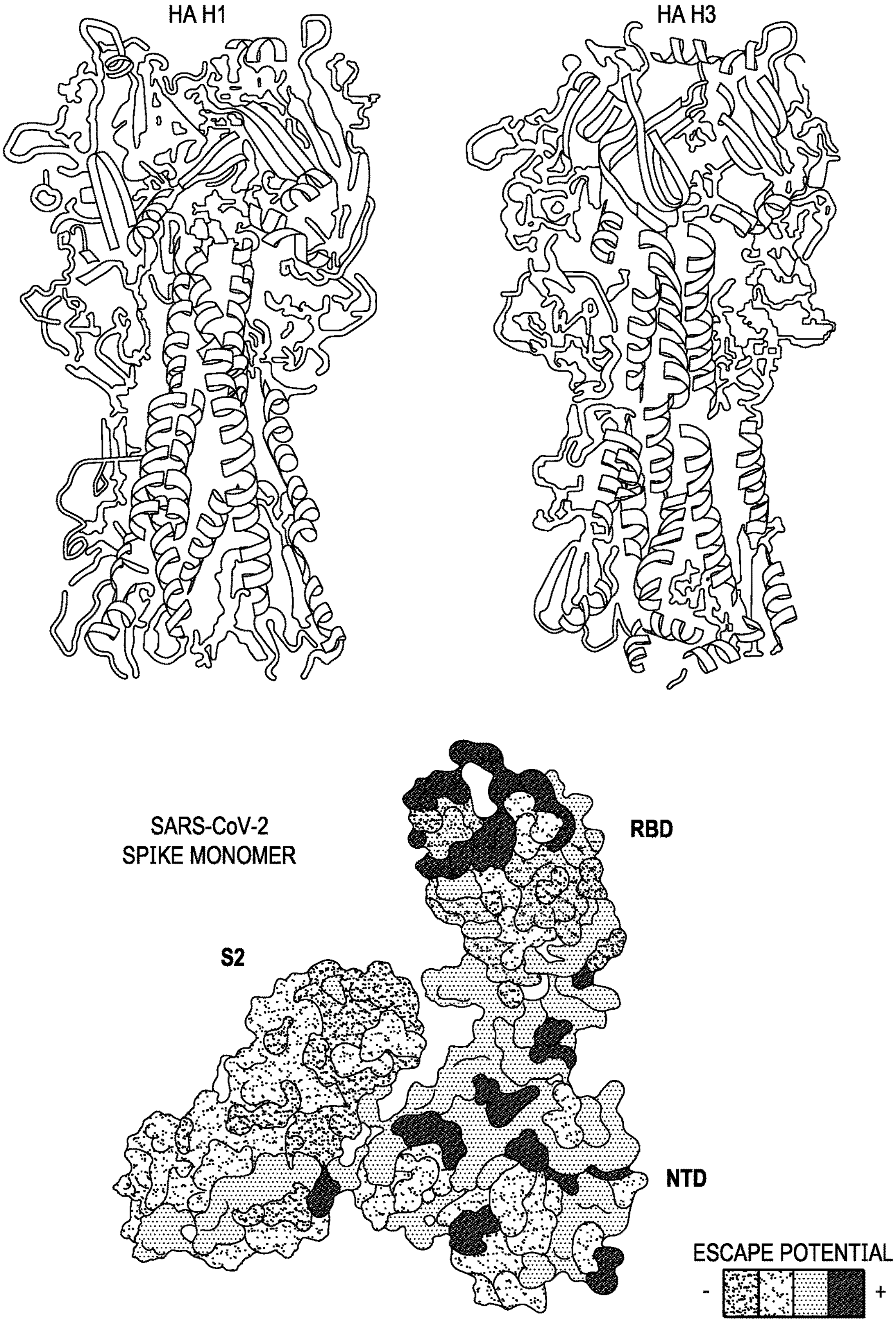
FIG. 5A and 5B depict various cartoon and surface visualizations of escape potential for several viral protein structures.
Figure 5B:
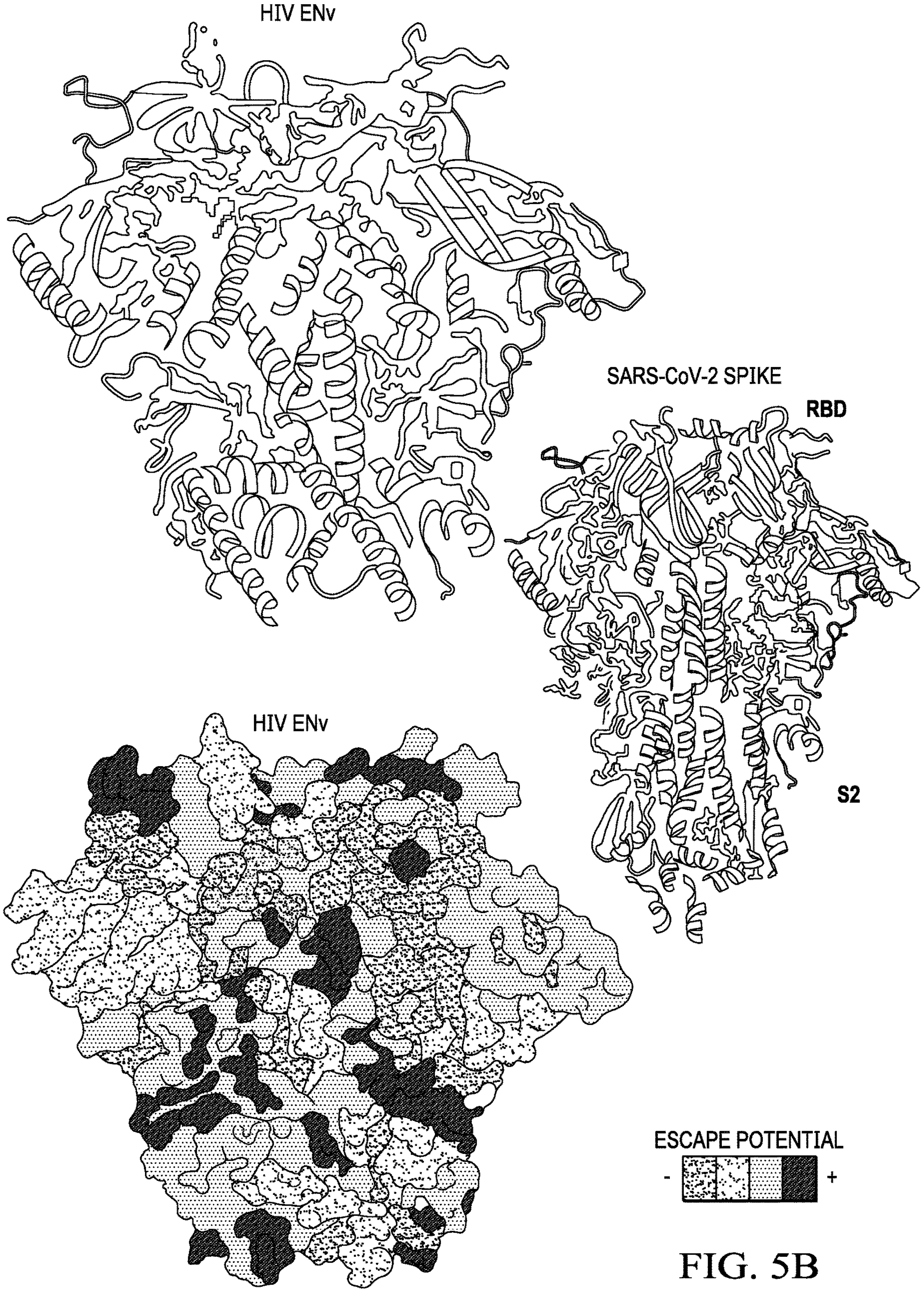

FIG. 5A and 5B depict various cartoon and surface visualizations of escape potential for several viral protein structures additional visualizations of protein structures. In particular, this figure depicts cartoon n illustrations of HA H1 and HA H3. It also depicts HIV Env as cartoon and surface oriented to illustrate the semantically-important inner domain. Further, the drawing also depicts views of SARS-CoV-2 Spike in monomeric (surface) and trimeric form (cartoon) illustrating S2 escape depletion.

As has been described, preferably a single model is used to simultaneously learn both semantics and grammaticality. After training the language model on a corpus of viral protein sequences from animals with homologous proteins, the language model learns a different internal representation for each sequence (based only on semantics, not grammaticality). CSCS is then used to predict which mutations to a viral protein lead to escape, and this is achieved without telling the model anything about known escape mutations. Thus, the technique herein provides for zero-shot prediction. For example, our model identifies significant escape potential in the head region of influenza HA but significant escape depletion in the stalk region, consistent with the current efforts to find antibodies that can broadly neutralize many different types of influenza by binding to the stalk. Similarly, for the SARS-CoV-2 Spike, the model predicts significant escape depletion in certain regions of the S2 subunit. Based on these predictions, antiviral therapeutics that target regions less prone to escape are then developed. For example, in the field of molecular modeling, docking is a method which predicts the preferred orientation of one molecule to a second when bound to each other to form a stable complex. Molecular docking one of the most frequently used methods in structure-based drug design. due to its ability to predict the binding-conformation of small molecule ligands to the appropriate target binding site. Using docking, a drug molecule is selected to target a low-escape protein region by simulating how well it binds or "docks" to the protein region, where that low-escape protein region is identified by the language model-based escape profiling technique of this disclosure. In this manner, the described methods improve these docking technologies. For vaccine design, the language model-based escape profiling herein facilitates selection of parts of the protein to go into a vaccine. An example technology of this type is called immunofocusing, and it is used to engineer antigens in order to produce antibodies with desired characteristics. Using the techniques herein, subregions of a protein that go into the vaccine are identified with more precision, thereby improving the efficiencies of the underlying technology. Docking and immunofocusing are representative underlying technologies that are improved by applying the language model-based escape profiling methods of this disclosure, but they are not intended to be limited. More generally, when designing therapeutics or vaccines, language modeling as described herein sheds light on those parts of proteins that are not prone to escape, thus enabling the modeling to act as a front-end technology solution that improves the efficiency or operation of the underlying antiviral therapeutic or vaccine design technology.

Other Methods and Materials

Models described herein were trained and evaluated with Tensorflow 2.2.0 and Python 3.7 on Ubuntu 18.04, with access to a Nvidia Tesla V100 PCIe GPU (32 GB RAM) and an Intel Xeon Gold 6130 CPU (2.10GHz, 768 GB of RAM). Using CUDA-based GPU acceleration, training on the influenza HA corpus required approximately 72 hours and evaluating all possible single-residue mutant sequences for a single strain required approximately 35 minutes. Training on the HIV Env corpus required approximately 80 hours and evaluating all possible single-residue mutant sequences required approximately 90 minutes. Training on the coronavirus spike corpus required approximately 20 hours and evaluating all possible single-residue mutant sequences required approximately 10 hours.

The following publicly-available datasets were used for model training: Influenza A HA protein sequences from the NIAID Influenza Research Database (IRD) (www.fludb.org); HIV-1 Env protein sequences from the Los Alamos National Laboratory (LANL) HIV database (www.hiv.lanl.gov); *Coronavidae* spike protein sequences from the Virus Pathogen Resource (ViPR) database (www.viprbrc.org/brc/home.spg?decorator=corona); SARS-CoV-2 Spike protein sequences from NCBI Virus (www.ncbi.nlm.nih.gov/labs/virus/vssi/); and SARS-CoV-2 Spike and other Betacoronavirus spike protein sequences from GISAID (www.gisaid.org/).

In one embodiment, the language model is trained to predict the observed amino acid residue at all positions in each sequence, using the remaining sequence as the input; one training epoch is completed when the model has considered all positions in all sequences in the training corpus. Each model is trained until convergence of cross entropy loss across one training epoch. The language models for HA, Env, and Spike were used to produce semantic embeddings for sequences within each language model's respective training corpus, where the semantic embedding procedure as described above. In particular, and using the Scanpy version 1.4.5 Python package, the Euclidean k-nearest neighbors (KNN) graph where each node corresponds to an embedded viral sequence (k=100 for influenza and HIV and k=20 for coronavirus) was first constructed. Based on the KNN graph, UMAP Python implementation as wrapped by Scanpy was used with default parameters to construct the two-dimensional visualizations. Also based on the same KNN graph, unsupervised clustering with Louvain community detection was performed with a resolution parameter of 1, also using the implementation wrapped by Scanpy, to cluster sequences within each viral corpus. Louvain cluster purity was evaluated with respect to a metadata class (e.g., host species or subtype) by first calculating the percent composition of each metadata class label (e.g., "H1" through "H16" for HA subtype) within a given cluster and using the maximum composition over all class labels as the purity percentage; this purity percentage for each Louvain cluster was calculate.

Escape potential is computed at each position within a given viral sequence by summing the value of the CSCS rank-based acquisition function (i.e., $a'(\tilde{x}_i; x)$) across all amino acids. These scores from the protein sequences of interest (used in the escape prediction validation experiments) are then mapped to three-dimensional structural loci. The enrichment or depletion of escape prediction scores within a given region of a protein sequence are quantified as follows. Define a region as a (potentially non-contiguous) set of positions. Head and stalk regions for HA were determined based on the coordinates used by Kirkpatrick et al. Region positions for Env were determined using the annotation provided by UniProt (ID: QN0S5) and hypervariable loops were determined as defined by the HIV LANL database. Region positions for SARS-CoV-2 were determined using the annotation provided by UniProt (ID: P0DTC2).

Generalizing, one or more of the machine learning techniques described herein are provided using a set of one or more computing-related entities (systems, machines, processes, programs, libraries, functions, or the like) that together facilitate or provide the described functionality described above. In a typical implementation, a representative machine on which machine learning software executes comprises commodity hardware, an operating system, an application runtime environment, and a set of applications or processes and associated data, that provide the functionality of a given system or subsystem. The functionality may be implemented in a standalone machine, or across a distributed set of machines.

One or more machine learning-based algorithms may be implemented in computer software as a set of computer program instructions executable in one or more processors, as a special-purpose machine. Representative machines on which the subject matter herein is provided may be hardware processor-based computers running an operating system and one or more applications to carry out the described functionality.

The model training may be provided as a service.

The technique herein leverages the principle that evolutionary selection is reflected in sequence variation. As such, CSCS as described herein may be applied beyond viral escape to different kinds of natural selection (e.g., T-cell selection) or drug selection. For example, CSCS and its components may be used to select components of a multivalent or mosaic vaccine. The techniques herein may also provide the foundation for more complex modelling of sequence dynamics. As such, distributional hypothesis from linguistics (in which co-occurrence patterns can model complex concepts and on which language models are based), may be used to extend the approach described herein.

Further, the language model-based escape profiling techniques herein are not limited to viral escape profiling. More generally, the techniques may be used to profile escape for any surface proteins that are highly mutagenic, e.g., the malaria parasite.

Still further, the notion of identifying escape potential with respect to a "region" of a protein sequence (or more generally, a genome or portion thereof) is not limited to a single region, as the technique may also facilitate identifying mutations from different regions, as well as epigenetic-type mutations.

Having described the subject matter herein, what we claim also is set forth below:

1. A method of escape profiling for therapeutic or vaccine development, comprising:

training a language-based model against training data comprising a corpus of protein sequences of a given protein to model an escape profile of the given protein, the escape profile representing, for one or more regions of the given protein, a relative escape potential of a mutation, the relative escape potential being derived as a function that combines both semantic change, wherein semantic change is a non-zero degree to which the mutation is recognized by the human immune system, and grammaticality, wherein grammaticality is a degree to which the mutation affects infectivity;

generating a visualization of the relative escape potential across the given protein, the visualization depicting areas of enrichment or depletion of escape potential;

based at least in part on the areas of enrichment or depletion of escape potential depicted in the visualization, identifying a region or sub-region of the given protein having an escape potential of interest; and outputting information regarding the region or sub-region to one of: a vaccine design workflow, and a therapeutic design workflow.

2. The method as described in claim 1 wherein the corpus of protein sequences of the given protein comprises copies of amino acid sequences from multiple host species.

3. The method as described in claim 1 wherein the language-based model is trained in an unsupervised manner, without data about known escape mutations.

4. The method as described in claim 1 wherein the escape potential of interest is a low escape potential, the method further including targeting the region or sub-region in the vaccine design workflow.

5. The method as described in claim 1 wherein the escape potential of interest is a high escape potential, the method further including targeting the region or sub-region in the therapeutic design workflow.

6. The method as described in claim 1 wherein the mutation is one of: a single mutation, and a combinatorial mutation.

7. The method as described in claim 1 wherein the function that combines both semantic change and grammaticality applies a weighting to a score representing one of: the semantic change, the grammaticality, and a combination of semantic change and grammaticality.

8. The method as described in claim 1 wherein identifying the region or sub-region of the given protein performs a constrained semantic change search (CSCS) to identify grammatical mutations to the given protein that induce high semantic change.

9. The method as described in claim 1 wherein the given protein is a viral protein that is one of: influenza hemagglutinin, HIV Env, and SARS-CoV-2 Spike.

* * * * *